United States Patent
Lee et al.

(10) Patent No.: US 9,828,394 B2
(45) Date of Patent: Nov. 28, 2017

(54) METHOD OF PREPARING DIALKYL-, DIARYL-, AND ALKYLARYL-DIHALOSILANES WITH HIGH SELECTIVITY IN A GRIGNARD COUPLING REACTION

(71) Applicant: Dow Corning Corporation, Midland, MI (US)

(72) Inventors: James Lee, Rochester, MI (US); Binh Thanh Nguyen, Midland, MI (US); Scott E. Pider, Midland, MI (US); Steven L. Umphrey, Midland, MI (US); Hanh Xuan Vo, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 14/775,816

(22) PCT Filed: Mar. 14, 2014

(86) PCT No.: PCT/US2014/027339
§ 371 (c)(1),
(2) Date: Sep. 14, 2015

(87) PCT Pub. No.: WO2014/152436
PCT Pub. Date: Sep. 25, 2014

(65) Prior Publication Data
US 2016/0031917 A1    Feb. 4, 2016

Related U.S. Application Data

(60) Provisional application No. 61/786,750, filed on Mar. 15, 2013.

(51) Int. Cl.
C07F 7/08    (2006.01)
C07F 7/12    (2006.01)

(52) U.S. Cl.
CPC ............... *C07F 7/125* (2013.01); *C07F 7/12* (2013.01); *C07F 7/122* (2013.01)

(58) Field of Classification Search
CPC ........................................................ C07F 9/08
USPC .......................................................... 556/480
See application file for complete search history.

(56) References Cited

U.S. PATENT DOCUMENTS

| 5,430,168 A | 7/1995 | Ferguson et al. |
| 6,541,651 B1 * | 4/2003 | Bedbury ................. C07F 7/122 260/665 G |
| 2003/0191238 A1 | 10/2003 | Bedbury et al. |
| 2012/0046488 A1 | 2/2012 | Willey et al. |

FOREIGN PATENT DOCUMENTS

| JP | H08208666 A | 8/1996 |
| JP | 2005514499 A | 5/2005 |
| JP | 2005521745 A | 7/2005 |
| JP | 3880619 B2 | 11/2006 |
| WO | WO9600709 A1 | 1/1996 |
| WO | WO03059966 A1 | 7/2003 |
| WO | WO03084967 A1 | 10/2003 |
| WO | 2006/083665 A1 | 8/2006 |

OTHER PUBLICATIONS

S. D. Rosenberg et al: "Preparation of Some Arylchlorosilanes with Arylmagnesium Chlorides," J. Org. Chem., Jan. 1, 1957 (Jan. 1, 1957), pp. 1606-1607.

* cited by examiner

Primary Examiner — Fereydoun G Sajjadi
Assistant Examiner — Kofi Adzamli
(74) Attorney, Agent, or Firm — Warner Norcross & Judd LLP (57) ABSTRACT

A method of making a diakyl-, diaryl-, or alkylaryl-dihalosilane in a Grignard coupling reaction with a high degree of selectivity is provided. More specifically, a Grignard reagent comprising an alkyl- or aryl-magnesium halide is allowed to react with an alkyl- or aryl-trihalosilane precursor or reagent to produce a product mixture of $R_2SiX_2$ and $R_3SiX$, wherein each R is independently selected to be an alkyl or aryl group and X is a halogen group, such that the $R_2SiX_2$ product is formed with a high degree of selectivity. High selectivity is defined as the mass ratio of $R_2SiX_2$ product to the $R_3SiX$ product that is formed in the reaction being greater than 7:1.

11 Claims, 8 Drawing Sheets

METHOD OF PREPARING DIALKYL-, DIARYL-, AND ALKYLARYL-DIHALOSILANES WITH HIGH SELECTIVITY IN A GRIGNARD COUPLING REACTION

CROSS-REFERENCE TO RELATED APPLICATIONS

This application is the National Stage of International Application Serial No. PCT/US2014/027339 filed on Mar. 14, 2014, designating the United States and published in English, which claims the benefit of the filing date under 35 U.S.C. §119(e) of U.S. Provisional Application No. 61/786, 750 filed Mar. 15, 2013, the entire contents of each of which are hereby incorporated herein by reference.

This disclosure relates generally to a method of making dihalosilanes and the use thereof. More specifically, this disclosure relates to the preparation of dialkyl-, diaryl-, or alkylaryl-dihalosilanes in a Grignard coupling reaction with a high degree of selectivity.

The statements in this section merely provide background information related to the present disclosure and may not constitute prior art. Dihalosilanes are generally used as precursors or reagents in the industrial production of a variety of silicone and polysilane compounds. For example, the demand for an alkylaryl-dihalosilane, such as phenylmethyldichlorosilane ($PhMeSiCl_2$), is steadily increasing for use in producing a variety of materials used in everyday life.

An example of a process that is generally used to prepare phenylmethyldichlorosilane ($PhMeSiCl_2$) is the reaction of a Grignard reagent, such as PhMgCl, with methyltrichlorosilane, $MeSiCl_3$ in a continuous stirred tank reactor (CSTR). This type of conventional process is usually optimized by using a higher concentration of $MeSiCl_3$ as compared to the Grignard reagent. In this manner, the likelihood of the Grignard reagent reacting with the $MeSiCl_3$ is greater than the likelihood of the Grignard reagent reacting with the $PhMeSiCl_2$ product to form diphenylmethylchlorosilane ($Ph_2MeSiCl$) as a by-product. Typically, at least a 3:1 mass ratio of $MeSiCl_3$ to PhMgCl is used as reactants in order to yield up to a 7:1 mass ratio of $PhMeSiCl_2$ to $Ph_2MeSiCl$ as products.

BRIEF SUMMARY OF THE INVENTION

This invention generally comprises a method of making dialkyl-, diaryl-, or alkylaryl-dihalosilane in a Grignard coupling reaction with a high degree of selectivity. This method comprises the steps of: providing a plug flow reactor (PFR), a continuous tube reactor (CTR), a piston flow reactor, or more than one continuous stirred tank reactor (CSTR) connected in series; providing a hydrocarbon solvent stream at a predetermined flow rate to the PFR; providing an alkyl- or aryl-trihalosilane stream at a predetermined flow rate to the PFR; providing a Grignard reagent stream comprising an alkyl- or aryl-magnesium halide at a predetermined flow rate to the PFR; allowing the solvent stream, alkyl- or aryl-trihalosilane stream, and Grignard reagent stream to combine to form a combined reactant stream; allowing the combined reactant stream to react at a temperature from about 10° C. to about 80° C. to form a product mixture comprising $R_2SiX_2$, $R_3SiX$, and a salt, wherein each R is independently selected to be an alkyl or aryl group derived from either the Grignard reagent or the alkyl- or aryl-trihalosilane, X is a halogen group, and the mass ratio of $R_2SiX_2$ to $R_3SiX$ in the product mixture is greater than 7:1; and, optionally, collecting the product mixture. In this method, the flow rate of the solvent stream, alkyl- or aryl-trihalosilane stream, and the Grignard reagent stream are selected so that the mass ratio of the alkyl- or aryl-trihalosilane to Grignard reagent in the combined reactant stream is at least 1.5:1 and the mass ratio of solvent to Grignard reagent in the combined reactant stream is at least 3:1. The mass ratio of $R_2SiX_2$ to $R_3SiX$ in the product mixture is alternatively greater than 12:1; alternatively, greater than 19:1; alternatively, greater than 25:1.

According to one aspect of the present disclosure, the reactor is a PFR that comprises at least one fluidic module, the solvent is toluene, the Grignard reagent is phenylmagnesium chloride (PhMgCl), the alkyl- or aryl-trihalosilane is methyltrichlorosilane ($MeSiCl_3$); and the product mixture formed comprises $PhMeSiCl_2$, $Ph_2MeSiCl$, and $MgCl_2$. Alternatively, the PFR is a Corning® Advanced Flow Glass Reactor™.

According to another aspect of the present disclosure, the method may further comprise the steps of: measuring a baseline pressure drop across the reactor prior to starting the Grignard reaction; monitoring the pressure drop across the reactor during the course of the Grignard reaction; and comparing the pressure drop across the reactor monitored during the course of the Grignard reaction to the baseline pressure drop in order to determine a change in the pressure drop. The change in pressure drop provides a measurement for the degree to which the reactor is plugged by the salt that has agglomerated and settled in the reactor or that has deposited on the walls in the reactor. When the reactor becomes plugged, the method may also comprise the steps of: stopping the Grignard reaction; removing the salt that is plugging the reactor; and restarting the Grignard reaction. One specific way of removing the salt that is plugging the reactor includes the steps of: isolating the plugged portion of the reactor from the rest of the reactor; flushing hydrocarbon solvent through the isolated portion of the reactor to remove the alkyl- or aryl-trichlorosilane; flushing water through the isolated portion of the reactor until all the salts are removed; flushing an alcohol through the isolated portion of the reactor to remove any residual water; flushing the hydrocarbon solvent through the isolated portion of the reactor again to purge the alcohol from the isolated portion; and reestablishing contact between the isolated portion of the reactor and the rest of the reactor.

During the course of the Grignard reaction, the combined reactant stream has a flow rate that is predetermined such that the residence time for the combined reactant stream in the reactor, is less than about 30 seconds; alternatively less than about 20 seconds. The residence time is defined as the average amount of time that the combined reactant stream resides within the reactor. In order to reduce the potential for salt agglomeration and settling in the reactor, the mass ratio of solvent to Grignard reagent may be selected to be greater than 5:1; alternatively, greater than 6:1. In addition, the Grignard reagent stream may be a solution that comprises the Grignard reagent dispersed in a solvent; wherein the amount of Grignard reagent present in the solution is less than 75 wt. %; alternatively less than 50 wt. %; alternatively, less than 25 wt. % based on the overall weight of the solution. The solvent used in the Grignard solution may be the same as the hydrocarbon solvent used in the Grignard reaction or it may be a solvent that is compatible or miscible the hydrocarbon solvent.

According to another aspect of the present disclosure a product mixture comprising $R_2SiX_2$ and $R_3SiX$ is formed according to the method described herein; wherein each R is independently selected to be an alkyl or aryl group, X is a halogen group, and the mass ratio of $R_2SiX_2$ to $R_3SiX$ in the product mixture is greater than 7:1; alternatively, greater than 12:1; alternatively, greater than 19:1; alternatively, greater than 25:1. This product mixture may be a mixture of $PhMeSiCl_2$ and $Ph_2MeSiCl$. The phenylmethyldichlorosilane in the product mixture may be isolated or collected.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

The following description is merely exemplary in nature and is in no way intended to limit the present disclosure or its application or uses. It should be understood that throughout the description, corresponding reference numerals indicate like or corresponding parts and features.

The present disclosure generally relates to a method of making dialkyl-, diaryl-, or alkylaryl-dihalosilane in a Grignard coupling reaction with a high degree of selectivity. More specifically, a Grignard reagent comprising an alkyl- or aryl-magnesium halide is allowed to react with an alkyl- or aryl-trihalosilane precursor or reagent to produce a product mixture of $R_2SiX_2$ and $R_3SiX$, wherein each R is independently selected to be an alkyl or aryl group and X is a halogen group, such that the $R_2SiX_2$ product is formed with a high degree of selectivity. High selectivity is defined as the mass ratio of $R_2SiX_2$ product to the $R_3SiX$ product that is formed in the reaction being greater than 7:1, alternatively, at least about 12:1, alternatively, at least about 19:1; alternatively, at least about 25:1; alternatively, up to about 97:1 when using a 3:1 mass ratio of the alkyl- or aryl-trihalosilane precursor to Grignard reagent; and up to about 130:1 when using a 5:1 mass ratio of the alkyl- or aryl-trihalosilane precursor to Grignard reagent with a solvent to Grignard reagent dilution of about 6:1. The high selectivity for $R_2SiX_2$ product is made possible by allowing the reaction to occur in a reactor, such as a plug flow reactor (PFR), a continuous tube reactor (CTR), a piston flow reactor, or more than one continuous stirred tank reactors connected in series, alternatively, a plug flow reactor, such as a Corning® Advanced Flow Glass Reactor. The $R_2SiX_2$ selectivity increases as the ratio of solvent to Grignard reagent increases because the Grignard reagent is more likely to react with alkyl- or aryl-trihalosilane rather than $R_2SiX_2$.

In order to more fully illustrate the concept, the invention is described throughout the following disclosure in terms of phenylmagnesium chloride (PhMgCl) as the Grignard reagent reacting with methyltrichlorosilane ($MeSiCl_3$) as the alkyl-trihalosilane to produce a mixture of phenylmethyldichlorosilane ($PhMeSiCl_2$) and diphenylmethylchlorosilane ($Ph_2MeSiCl$), such that $PhMeSiCl_2$ is formed with a high degree of selectivity. One skilled-in-the-art will understand that this concept can be extended to the reaction of other alkyl- or aryl-magnesium halides as Grignard reagents with other alkyl- or aryl-trihalosilane reagents to form the corresponding dialkyl-, diaryl-, or alkylaryl-dichalosilanes without exceeding the scope of the present disclosure. Several examples of Grignard reagents, include but are not limited to, ethylmagnesium chloride, cyclopentylmagnesium bromide, methylmagnesium iodide, isopropylmagnesium chloride, butylmagnesium chloride, phenylmagnesium chloride, 3,4,5-trifluorophenylmagnesium bromide, The alkyl- or aryl-trihalosilane may be any molecule known in the art having the formula $RSiX_3$ wherein R is an alkyl group having from 1 to about 10 carbon atoms, alternatively, 1 to about 4 carbon atoms, or an aryl group having about 6 to about 24 carbon atoms, alternatively about 6 to about 12 carbon atoms, and wherein X is a halogen atom, such as chlorine, bromine, or iodine. Several examples of alkyl- or aryl-trihalosilanes, include but are not limited to, methyltrichlorosilane, ethyltribromosilane, and phenyltrichlorosilane, According to one aspect of the present disclosure, the chemical reaction as shown in Equation 1 can be described as a coupling reaction that occurs between a Grignard reagent (PhMgCl) and trichlorosilane ($MeSiCl_3$) dissolved or dispersed in a solvent to produce $PhMeSiCl_2$ and a magnesium salt. The magnesium salt and the solvent are selected, such that the magnesium salt precipitates from solution as a solid. Alternatively, the solvent may be an aromatic hydrocarbon, alternatively, toluene; and the magnesium salt is magnesium chloride ($MgCl_2$). A side reaction can occur between the Grignard reagent and the $PhMeSiCl_2$ product that leads to the formation of $Ph_2MeSiCl$ as a by-product according to Equation 2. This type of chemical reaction is known as a series-parallel reaction. In order to increase the selectivity of the desired product, in this case PhMeSiCl$_2$, the reaction performed according to the method of the present disclosure is allowed to occur in a plug flow reactor a continuous tube reactor (CTR), a piston flow reactor, and more than one continuous stirred tank reactor (CSTR) connected in series; alternatively, in a Corning® Advanced Flow Reactor™.

Eq. 1

Eq. 2

The method of making dialkyl-, diaryl-, or alkylaryl-dihalosilanes in a Grignard coupling reaction with a high degree of selectivity generally comprises the steps of: providing a reactor, selected as one from the group of a plug flow reactor (PFR), a continuous tube reactor (CTR), a piston flow reactor, and more than one continuous stirred tank reactor (CSTR) connected in series; providing a hydrocarbon solvent stream at a predetermined flow rate to the reactor; providing an alkyl- or aryl-trihalosilane stream at a predetermined flow rate to the reactor; providing a Grignard reagent stream, comprising an alkyl- or aryl-magnesium halide, at a predetermined flow rate to the reactor; allowing the solvent stream, alkyl- or aryl-trihalosilane stream, and Grignard reagent stream to combine to form a combined reactant stream; allowing the combined reactant stream to react at a temperature from about 10° C. to about 80° C. to form a product mixture comprising $R_2SiX_2$, $R_3SiX$, and a salt, wherein each R is independently selected to be an alkyl or aryl group, X is a halogen group, and the mass ratio of $R_2SiX_2$ to $R_3SiX$ in the product mixture is greater than 7:1; and optionally, collecting the product mixture. In this method the flow rate of the solvent stream, alkyl- or aryl-trihalosilane stream, and the Grignard reagent stream are selected so that the mass ratio of the alkyl- or aryl-trihalosilane to Grignard reagent in the combined reactant stream is greater than or equal to 1.5:1 and the mass ratio of the solvent to Grignard reagent in the combined reactant stream is greater than or equal to 3:1.

The hydrocarbon solvent may any aliphatic or aromatic solvent in which a Grignard reaction is capable of being performed. Several specific examples of a hydrocarbon solvent, include but are not limited to, benzene, toluene, xylene, hexane, n-heptane, octane, cyclohexane, and cycloheptane, to name a few.

Figure 1:
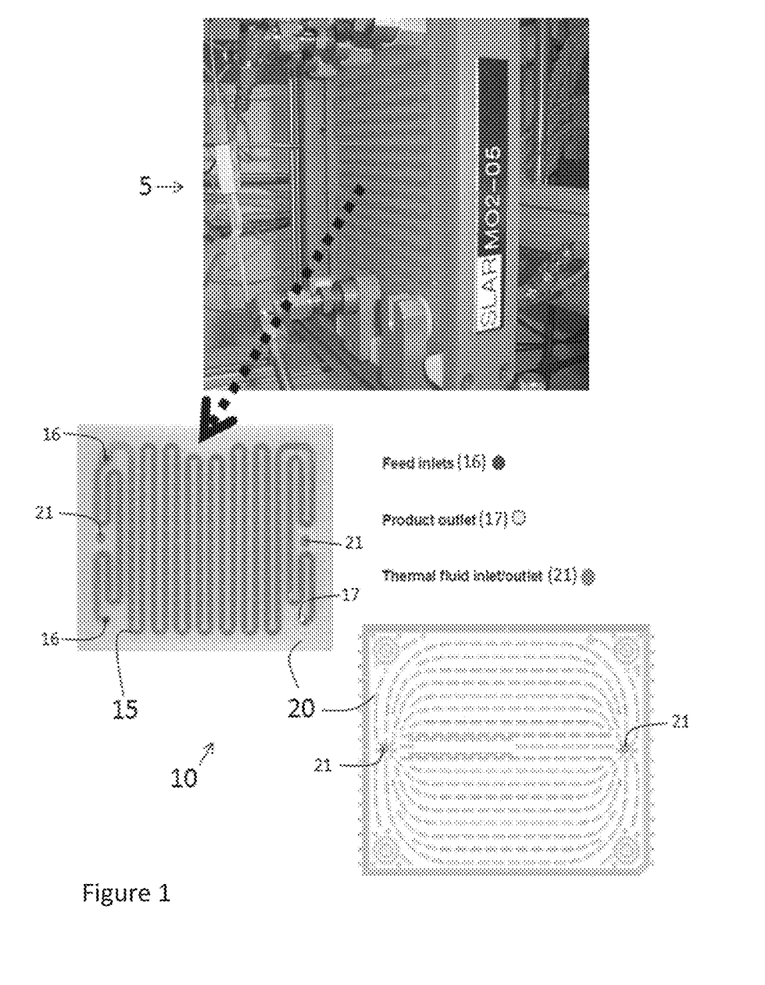
FIG. 1 is a schematic representation of a plug flow reactor (PFR) comprising a SJAR-type fluidic module.

In a plug flow reactor (PFR), one or more fluid reagents are pumped through a pipe or tubular component. The chemical reaction proceeds as the reagents flow or travel through the PFR. In this type of reactor, the changing reaction rate creates a gradient with respect to the distance traversed. In other words, at the inlet to the PFR, the reaction rate is usually very high, but as the concentration of the reagents decrease and the concentration of the product(s) increases as the reaction mixture flows through the PFR, the reaction rate begins to slow or decrease. Referring to FIG. 1, an example of a PFR 5 is shown that comprises one or more fluidic modules 10. A specific example of such a PFR is a Corning® Advanced Flow Glass Reactor™. Each fluidic module 10 comprises one fluidic layer dedicated to the reaction 15 and 2 fluidic layers (located on both sides of the reaction layer 15) dedicated to the circulation of a heat transfer fluid 20 that provides temperature control during the reaction via heat exchange. The reaction layer 15 includes at least one inlet 16 and at least one outlet 17 through which the reactants and products of the Grignard reaction may enter and exit the fluidic module 10. Similarly, the thermal layer 20 includes at least one inlet and outlet 21 through which the heat transfer fluid can flow.

Figure 2:
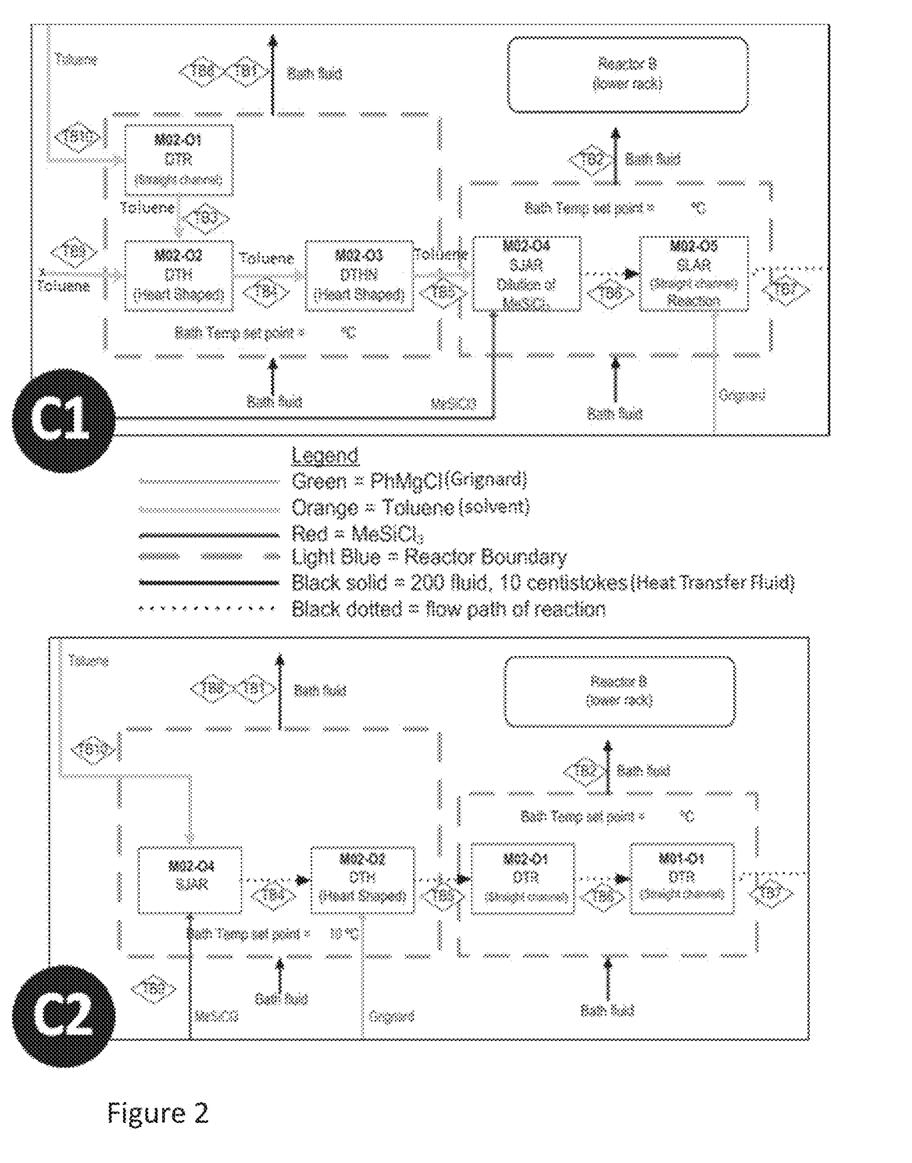
FIG. 2 is a schematic representation of two PFR configurations (C1 & C2) used to perform the Grignard reaction according to the teachings of the present disclosure.

Referring now to FIG. 2, two different configurations (C1 & C2) for the fluidic module 10 in a PFR 5 are shown. Each of these configurations is utilized to perform the Grignard reaction according to the teachings of the present disclosure. One skilled in the art will understand that these two configurations (C1 & C2) using different types or designs of fluidic modules 10 in the PFR 5 are used throughout the disclosure in order to more fully illustrate the concept and that the use of other fluidic modules 10, as well as other types of plug flow reactors, continuous tube reactors (CTR), piston flow reactors, or more than one continuous stirred tank reactors (CSTR) connected in series are contemplated to be within the scope of the present disclosure.

The main difference between the two PFR reactor configurations shown in FIG. 2 is the number and type of fluidic modules 10 utilized. In configuration C1, five different fluidic modules are utilized with one fluidic module being used after the Grignard reagent is mixed with the alkyl- or aryl-trihalosilane. In comparison, configuration C2 utilizes four different fluidic modules 10 with three modules being used after the Grignard reagent and alkyl- or aryl-trihalosilane are mixed. Each of the different fluidic modules 10 utilized in the two different PFR configurations (C1 & C2) is commercially available from Corning Incorporated, Corning, N.Y. for use in a Corning® Advanced Flow Glass Reactor™.

The residence time for the reaction in the PFR 5, continuous tube reactor (CTR), piston flow reactor, or more than one continuous stirred tank reactor (CSTR) connected in series; alternatively, in the Corning® Advanced Flow Glass Reactor™, depends on a multiple of factors including the size of the channels, pipes, or tubes, as well as the flow rate of the reaction mixture through the reactor. A residence time in the reactor in the range of about 20 to about 30 seconds corresponds to the situation wherein the Grignard reagent is completely consumed during the reaction. However, this length of residence time may also lead to at least partial plugging of the reactor due to the amount of magnesium salt that precipitates during the reaction. In a plug flow reactor, the solid magnesium salt may precipitate on the walls of the reactor and need to be periodically cleaned or removed. Thus shorter residence times may be utilized to reduce the need to remove the salt deposits as often.

The flow rate of the alkyl- or aryl-trihalosilane stream and the Grignard reagent stream can be predetermined so that the residence time for the combined reactant stream in the reactor is less than about 30 seconds, alternatively, less than about 20 seconds. Residence time is defined as the average time that the combined reactant stream resides within the reactor. The flow rates may be predetermined based on the desired residence time and the volume of the reactor. For example, in configuration C1, a residence time of 4.8 seconds is achieved at a 100 ml per minute flow rate with the overall reactor volume being on the order of about 8 ml. In configuration C2, a longer residence time of 15.6 seconds is achieved at a flow rate of 100 ml per minute with the reactor volume being on the order of about 26 ml.

The Grignard coupling reaction produces metal salts, such as magnesium chloride (MgCl$_2$), as a by-product. Due to the narrow channels in a reactor, there is the possibility that the reactor could plug due to the formation of the MgCl$_2$ salts. According to one aspect of the present disclosure, a possible method of cleaning the reactor system is to flush the reactor with water in order to dissolve the deposited salts. However, in this case, the reactor system must be dried prior to running the Grignard coupling reaction due to the sensitivity of the alkyl- or aryl-trihalosilane reagent to hydrolysis.

An experiment was run in a PFR 5 at 35° C. using a 3:1 MeSiCl$_3$:PhMgCl ratio for a long residence time of 2 minutes in order to ensure that all of the Grignard reagent reacted and the maximum amount of magnesium chloride salt was formed to at least partially plug the rector. The pressure drop was measured to be over 100 psig and kept continuing to increase during the run, indicating that the salts were building up and beginning to restrict the flow. The reactor should be cleaned when the pressure drop across the reactor increases by at least 50%; alternatively, by 100% or more; alternatively, by 150% or more. The Grignard reagent (e.g., PhMgCl) and alkyl- or aryl-trihalosilane (e.g., MeSiCl$_3$) flow are immediately stopped with only the flow of the hydrocarbon solvent (e.g., toluene) being allowed to continue through the reactor. Samples of the solvent flushed through the reactor are analyzed using gas chromatography to determine the amount of MeSiCl$_3$ present. When the amount of MeSiCl$_3$ is measured to be less than about 0.1%, the reactor is then flushed with water for several minutes in order to dissolve and remove all of the deposited magnesium salt.

After water has been run through a fluidic module of the PFR system, an alcohol, such as isopropanol (IPA) is pumped through the fluidic module using a peristaltic pump in order to remove any residual water present on the reactor walls. The fluidic module is then flushed with the hydrocarbon solvent and gas chromatography is used to analyze the hydrocarbon solvent in order to make sure that only the solvent is present in the reactor (e.g., no residual water or IPA). The fluidic module is then reconfigured with the rest of the PFR system and the solvent is flushed through the lines. The baseline pressure drop curve is re-measured to ensure that that the reactor is no longer plugged.

According to another aspect of the present disclosure, in order to prevent the salts from agglomerating and settling or depositing on to the glass walls of the reactor, a high flow rate is utilized. For example, a flow rate of 100 mL/min or more can be used to ensure that the magnesium salts will not agglomerate and settle in the reactor or deposit onto the walls of the reactor when the reactor has an overall volume of about 26 mL or less. In addition, a high flow rate allows for better mixing, which will not only improve the selectivity results for the reaction, but also help to suspend the salts in the solution and prevent them from agglomerating and settling out. Alternatively, a lower flow rate may be utilized provided the PFR is cleaned after a desired number of runs are completed. Acceptable lower flow rates for use in a PFR having a volume of 26 mL or less include those within the range of about 10 mL/min to 99 mL/min; alternatively, between about 25-99 mL/min; alternatively, between about 50-99 mL/min; and alternatively, between about 75-99 mL/min. One skilled in the art will understand how to scale the high and low flow rates described above for reactors that comprise a larger volume.

According to yet another aspect of the present disclosure, the severity of the magnesium salts agglomerating and settling in the reactor or depositing on the reactor walls can be reduced by increasing the ratio of the solvent to PhMgCl utilized or running the reaction at a lower temperature. A solvent to PhMgCl ratio of 6:1 or greater dilutes the concentration of the magnesium salts formed during the reaction, thereby, reducing the risk of plugging the reactor. The temperature of the reaction was varied in several experiments using the same reactor. At a reaction temperature of 80° C., the reactor was observed to plug almost instantly during the first few runs through the reactor. However, at a reaction temperature of 10° C., virtually no plugging was observed even after four runs through the reactor. This means that the rate at which magnesium salts are produced in the Grignard reaction is heavily dependent on the temperature of the reaction, which is dictated by the temperature of the heat exchanger fluid.

A process for removing a plug from a PFR 5, such as the Corning® Advanced Flow Glass Reactor™, is comprised of the steps of: flushing hydrocarbon solvent through the PFR and lines; isolating the plugged fluidic module from the PFR; flushing the solvent through the plugged fluidic module to remove the alkyl- or aryl-trihalosilane; flushing water through the fluidic module until all the magnesium salts are removed; flushing isopropyl alcohol (IPA) through the fluidic module to remove residual water; flushing the hydrocarbon solvent through the fluidic module again to purge the IPA from the system; and reestablishing contact between the fluid module and the rest of the PFR.

The following specific embodiments are given to illustrate the use of method according to the teachings of the present disclosure and should not be construed to limit the scope of the disclosure. Those skilled-in-the-art, in light of the present disclosure, will appreciate that many changes can be made in the specific embodiments which are disclosed herein and still obtain alike or similar result without departing from or exceeding the spirit or scope of the disclosure. One skilled in the art will further understand that any properties reported herein represent properties that are routinely measured and can be obtained by multiple different methods. The methods described herein represent one such method and other methods may be utilized without exceeding the scope of the present disclosure.

Example 1—PFR System Selection and Operation

A PFR system, such as the Corning@ Advanced Flow Glass Reactor™, is a modular reactor design with an assortment of different fluidic modules (plates) that allows for different reactor configurations. Changing the configuration will alter the mixing parameters, residence time, feed locations, and heat transfer. Due to the possibility of salt plugging, the first PFR comprises a single fluidic module (SLAR-type or design, see FIG. 1) for the reaction to take place which includes a straight through channel without any narrow cavities apart from the injection point. This PFR configuration is also shown in FIG. 2 as configuration C1. Toluene enters the first plate (M02-O1), MeSiCl$_3$ is introduced in the second to last plate (M02-O4), and then the Grignard reagent is introduced in the very last plate (M02-O5). The temperature control bath or heat transfer fluid for the first set of fluidic modules or plates is turned off, and the temperature control bath associated with the last two reactors are varied, such that they approach the desired reaction temperature. Configuration C1 results in a 4.8 second residence time at a 100 mL/min flow rate.

Figure 3:
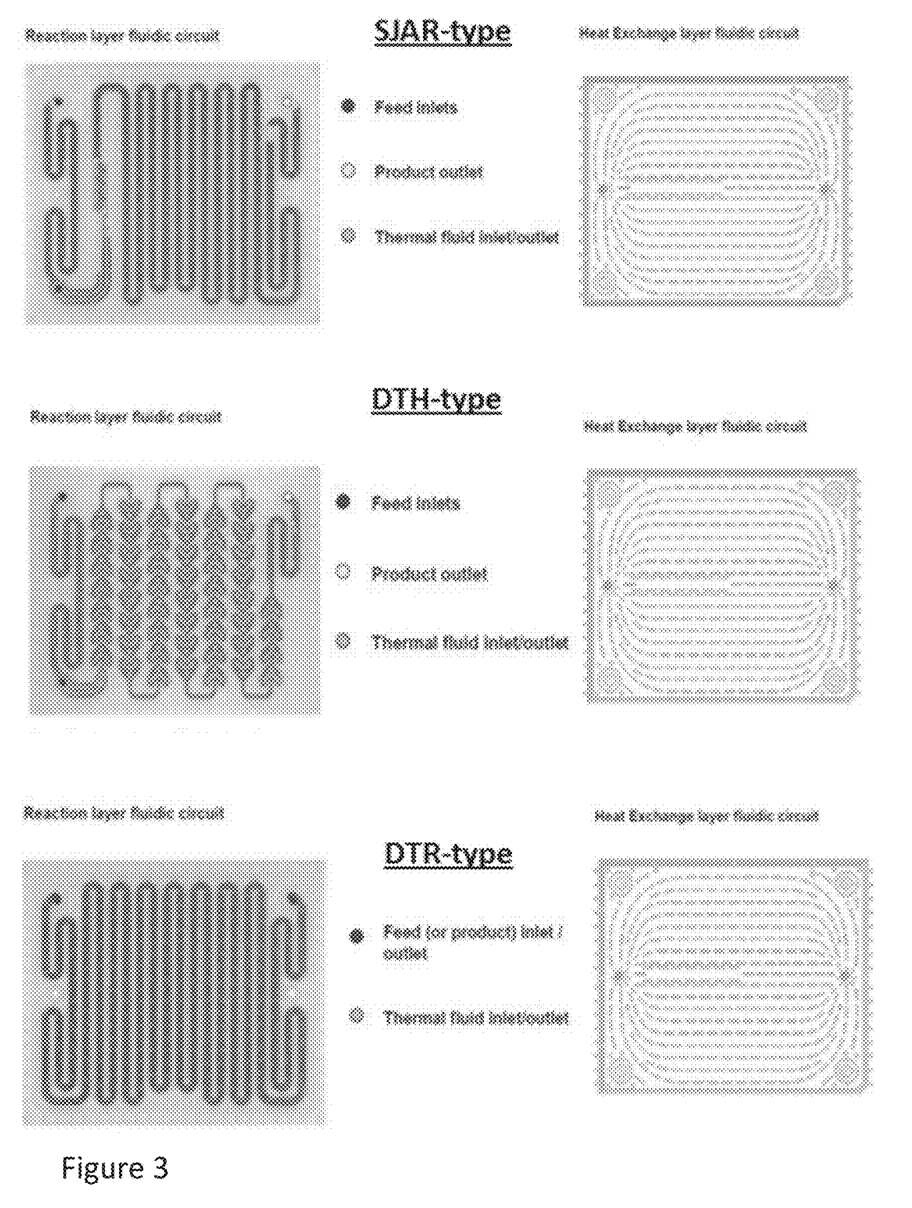
FIG. 3 is a schematic representation of SLAR-type, DTH-type, and DTR-type fluidic modules for use in a PFR.

The second PFR configuration C2 is used to obtain a longer residence time for the reaction. Since the flow rate cannot be decreased without increasing the likelihood of plugging and worsening the mixing, the selected way of increasing residence is to add more fluidic plates or modules. The second PFR configuration C2 comprises two plates (SJAR-type and DTH-type) to mix the reactants together at a low temperature (i.e., salts do not form in significant quantities at this lower temperature) and then a third and fourth plate for temperature control and to increase residence time (both DTR-type). The plate type or design described herein as SJAR-type or DTH-type refers to fluid modules that are commercially available from Corning Incorporated, Corning, N.Y., the general shape of which are shown in FIG. 3. Toluene and $MeSiCl_3$ are introduced in the very first plate (M02-O4) and then the Grignard reagent is introduced in the second plate (M02-O2) for adequate mixing; these two plates are operated at 10° C. The reactants then enter the last two plates (M02-O1 and M01-O1) to build residence time, and the temperature for these plates is varied to the desired temperature by controlling the bath temperature. This configuration C2 is shown in FIG. 2B. Configuration C2 yields a 15.6 second residence time at a flow rate of 100 mL/min.

When possible, connections between materials are made using 316SS Swagelok compression fittings and tubing, with Teflon tubing used to connect the manifolds to the PFR. The fluidic modules on the other hand require special fittings. The fluidic modules themselves are glass, but DuPont Kalrez™ O-rings supply the sealing surface between 316SS and the glass. A polyether ether ketone (PEEK) material is utilized in the connection. Typical tubing sizes for the reactor setup are 1/8" outer diameter tubing.

The supply of reagents to the PFR system was performed by Teledyne Isco 1000D positive displacement syringe pumps. The pumps are constructed of Nitronic 50 alloy (similar to 316SS) with PTFE seals. The pumps are limited in pressure to 250 psig, which is the limit of the Corning Advanced Flow Glass Reactor™. Three 1000 mL Teledyne Isco pumps were used: one for toluene, one for $MeSiCl_3$, and one for the Grignard reagent.

The temperature of the PFR system was maintained using a Thermo-Fisher Neslab NTE-7 recirculating bath. The fluid used in the bath was Dow Corning 200 fluid® 10 centistoke viscosity. The bath was set to a particular temperature and then automatically adjusted to maintain this temperature. Temperature control was provided by a Camile laboratory system via thermocouples located at various locations in between the fluidic modules; data is collected every 10 seconds. Although glass is not an efficient conductor of heat, the large amount of surface area gives the Corning reactor excellent heat transfer capabilities. No major temperature increases were noted during the reaction. Pressures were monitored via the integrated pressure sensors of the pumps as well as various pressure gauges located throughout the system.

Example 2—Performing Experimental Runs & Sampling

A total of 25 experimental runs using the PFR 5 described in Example 1 corresponding to configurations C1 or C2 were conducted as described in Table 1. During each experimental run a sample of the reaction mixture was collected and analyzed. Run No.'s 1-18 were conducted using PFR configuration C1 and Run No.'s 19-25 were conducted using PFR configuration C2. The 16 second residence time (Run No's 10-12) using configuration C1 was obtained by lowering the flow rate from 100 mL/min to 30 mL/min. The temperature for configuration C2 corresponds to the second bath temperature as the first bath temperature was consistently kept at 10° C. In each of the reactor configurations, at least about four passes were conducted in an experimental run at a single temperature before the deposition of magnesium salt necessitates the cleaning of the reactor.

TABLE 1

Summary of Experimental Runs.

| Run | Temperature | Ratio of MeSiCl3:Grignard | Residence Time (seconds) | # Samples Collected & Analyzed | PFR Configuration |
|---|---|---|---|---|---|
| 1 | 35° C. | 3:1 | 4.8 | 4 | C1 |
| 2 | 35° C. | 2:1 | 4.8 | 4 | C1 |
| 3 | 35° C. | 1.5:1 | 4.8 | 4 | C1 |
| 4 | 35° C. | 1:1 | 4.8 | 4 | C1 |
| 5 | 55° C. | 3:1 | 4.8 | 4 | C1 |
| 6 | 55° C. | 2:1 | 4.8 | 4 | C1 |
| 7 | 55° C. | 1.5:1 | 4.8 | 4 | C1 |
| 8 | 55° C. | 1:1 | 4.8 | 4 | C1 |
| 9 | 80° C. | 3:1 | 4.8 | 3 | C1 |
| 10 | 35° C. | 3:1 | 16 | 4 | C1 |
| 11 | 35° C. | 2:1 | 16 | 4 | C1 |
| 12 | 80° C. | 3:1 | 16 | 3 | C1 |
| 13 | 10° C. | 3:1 | 4.8 | 4 | C1 |
| 14 | 10° C. | 2:1 | 4.8 | 4 | C1 |
| 15 | 10° C. | 1.5:1 | 4.8 | 4 | C1 |
| 16 | 10° C. | 1:1 | 4.8 | 4 | C1 |
| 17 | 10° C. | 5:1 | 4.8 | 4 | C1 |
| 18 | 35° C. | 5:1 | 4.8 | 4 | C1 |
| 19 | 10° C. | 3:1 | 15.6 | 4 | C2 |
| 20 | 10° C. | 2:1 | 15.6 | 4 | C2 |
| 21 | 10° C. | 1.5:1 | 15.6 | 4 | C2 |
| 22 | 10° C. | 1:1 | 15.6 | 4 | C2 |
| 23 | 35° C. | 3:1 | 15.6 | 4 | C2 |
| 24 | 35° C. | 2:1 | 15.6 | 4 | C2 |
| 25 | 35° C. | 1.5:1 | 15.6 | 4 | C2 |

In each experimental run (No.'s 1-25), anhydrous toluene was supplied by 4 L containers from Fischer and an 18 L Pure-Pac™ cylinder from Sigma Aldrich Company. $MeSiCl_3$ was supplied from a cylinder and the Grignard reagent was supplied by a gallon container as well. The toluene and Grignard reagent containers were loaded into the pumps under a nitrogen blanket using ¼" Teflon tubing. The MeSiCl$_3$ cylinder and the toluene cylinder were directly connected to the pump for continuous loading.

The Grignard reagent was tested prior to use in order to identify the characteristics of the reagent solution utilized. The test consists of quenching a sample of the reagent with methanol to convert the Grignard reagent to benzene and then analyzing the sample using gas chromatography (GC). Another sample was then tested by GC using tetraethoxysilane in order to compare the amount of benzene in this sample to the quenched sample. The difference in benzene wt. % corresponds to the concentration of Grignard reagent in the sample. The first Grignard sample contained 20.1 wt. % Grignard reagent (the remaining wt. % being primarily diethyl ether) and the second Grignard sample contained 23.4 wt. % Grignard reagent based on the total weight of the Grignard solution.

Samples taken from each experimental run were handled in an air-free environment under a nitrogen blanket and then centrifuged to separate the liquid phase from the solid phase. The liquid portion was analyzed by gas chromatography (GC). The data plotted was always the last sample taken from the experimental run, usually the 4$^{th}$ sample (some runs only contained 3 samples), under the assumption that the system has reached steady state at this point. This sample was always run on the GC the same day it was taken to ensure the integrity of the sample.

Figure 4:
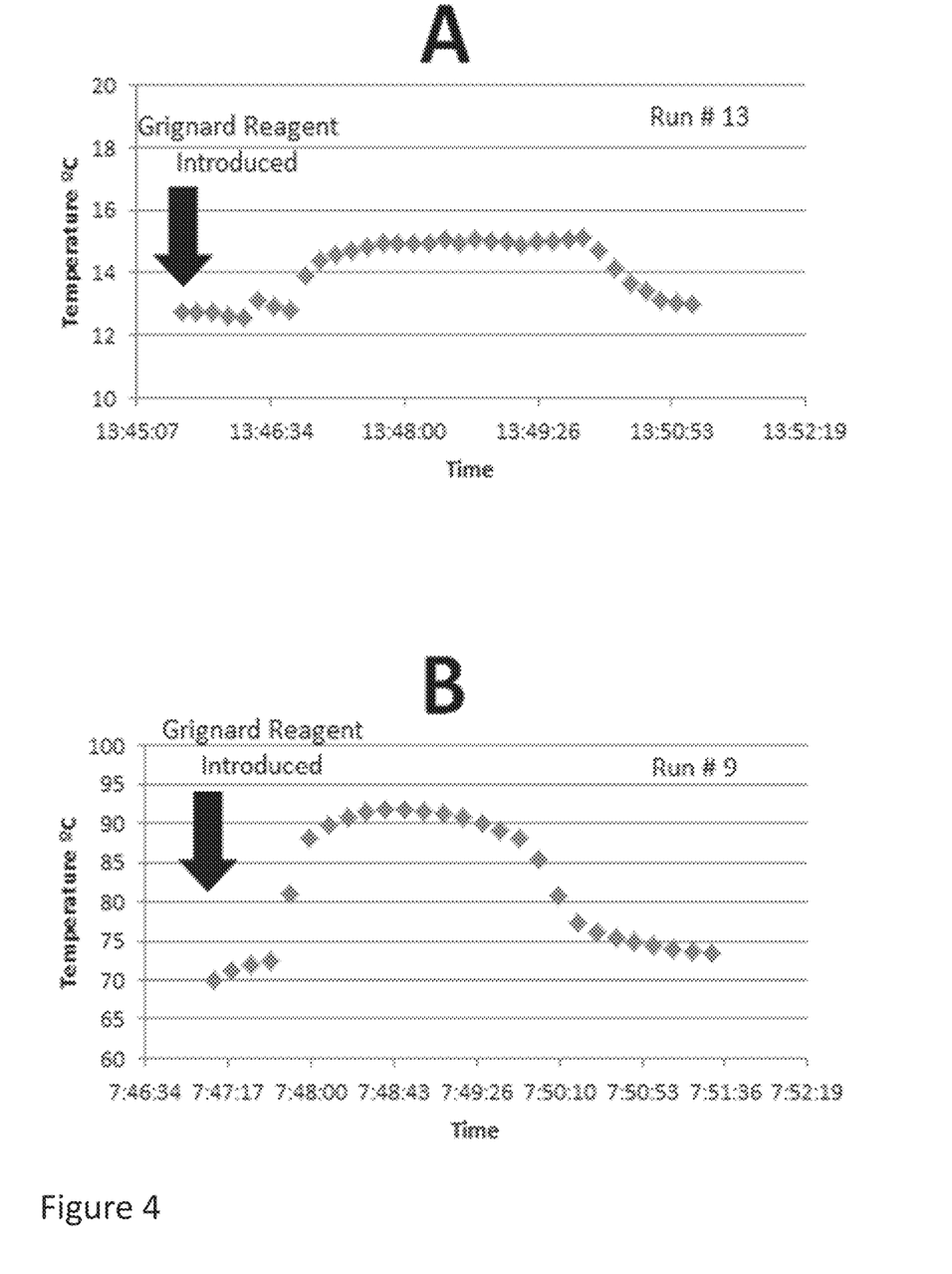
FIG. 4A is a graph of the outlet temperature of the PFR, configuration C1, as measured in Run No. 13 plotted as a function of time.
FIG. 4B is a graph of the outlet temperature of the PFR, configuration C1, as measured in Run No. 9 plotted as a function of time.

The Grignard coupling reaction is highly exothermic, with an adiabatic exotherm on the order of 138.9° C. However, the Corning® Advanced Flow Glass Reactor™ has extremely high heat transfer capabilities due to the large amount of surface area available for heat transfer. Referring to FIGS. 4A and 4B, during the reaction in the PFR, only small changes in temperature can be measured after the reaction begins as shown by the outlet temperature of the reactor after the Grignard reagent is introduced in to the system for Run No.'s 13 (FIG. 4A) and 9 (FIG. 4B). In each experimental run, the reaction temperature was maintained at the desired temperature by setting the heat transfer fluid (e.g., bath temperature) used in the fluidic modules at the desired temperature. The desired temperature ranged from about 10° C. to about 80° C. as described for the different experimental runs in Table 1.

The flow rates for the three reagent feed streams: solvent (e.g., toluene), MeSiCl$_3$, and the Grignard reagent (e.g., PhMgCl) are adjusted to provide a desired mass ratio of solvent to Grignard reagent and MeSiCl$_3$ to Grignard reagent. The toluene to PhMgCl mass ratio is maintained at least at 3:1 in order to reduce the risk of salt agglomeration and plugging of the PFR; alternatively, this mass ratio is at least 5:1, alternatively, at least 6:1. The mass ratio of MeSiCl$_3$ to PhMgCl was varied in the experimental runs from 5:1 (Run No.'s 17-18), 3:1 (Run No.'s 1, 5, 9-10, 12-13, 19, & 23), 2:1 (Run No.'s 2, 6, 11, 14, 20, & 24), 1.5:1 (Run No.'s 3, 7, 15, 21, & 25), and 1:1 (Run No.'s 4, 8, 16, & 22).

The Grignard reagent may be considered to be a Grignard reagent solution in that it is usually premixed with a predetermined amount of a solvent to assist in its transfer into the PFR. The solvent used in the Grignard solution may be the same as the hydrocarbon solvent used in the Grignard reaction or it may be a solvent that is compatible or miscible with the hydrocarbon solvent. Several specific examples of solvents used to form Grignard solutions include dialkyl ethers, such as dimethyl ether, diethyl ether, chlorobenzene (PhCl) tetrahydrofuran (THF) methyl n-propyl ether (MPE) tetrahydropyran (THP) 2,3-dihydrofuran (DHF), furan, benzene, 2-methyl tetrahydrofuran (2-MeTHF), and cyclopentyl methyl ether (CPME). The amount of the Grignard reagent in the precursor solution is less than about 75 wt. %; alternatively, less than about 50 wt. %; alternatively, less than about 25 wt. % based on the overall weight of the solution. For example, in Run No. 19, the flow rate of toluene, MeSiCl$_3$, and the Grignard solution (23.4 wt. % PhMgCl) was held at 40.556 mL/min, 22.319 mL/min, and 37.125 mL/min in order to provide an overall flow rate of 100 mL/min and to maintain the mass ratio of toluene to PhMgCl at 6:1 and the mass ratio of MeSiCl3 to PhMgCl at 3:1.

In each experimental run the reaction temperature was maintained at a desired temperature that is within the range of about 10° C. to 80° C. The trial (Run No. 12) conducted at 80° C. resulted in the completion of only 3 passes through the reactor prior to the reactor having to be cleaned due to salt agglomeration. The high temperature of 80° C. or more causes the salts to form extremely quickly in the PFR system.

A baseline differential pressure drop (ΔP) is generated for each PFR prior to use by flushing the solvent, e.g., toluene, through the PFR at different flow rates. Since there is a potential for salt build-up to occur during the reaction, which may result in the PFR becoming plugged, the measurement of ΔP during the course of the reaction can be used to compare against the measured baseline data. This comparison provides an on-going estimate as to the extent to which the PFR is becoming plugged. In Tables 2 and 3 the baseline differential pressure drop obtained for PFR configurations C1 and C2 are provided, respectively. The pressure drop across configuration C2 is shown to be greater than the pressure drop across configuration C1 even though there is one fewer fluidic module 10 used in the construction of the PFR (see FIG. 2).

TABLE 2

Baseline Differential Pressure Drop Across PFR Configuration 1

| Toluene Flow Rate (mL/min) | Differential Pressure (psig) |
| --- | --- |
| 0 | 0 |
| 30 | 5 |
| 50 | 10 |
| 75 | 20 |
| 100 | 34 |

TABLE 3

Baseline Differential Pressure Drop Across PFR Configuration C2

| Toluene Flow Rate (mL/min) | Differential Pressure (psig) |
| --- | --- |
| 0 | 1 |
| 30 | 5 |
| 50 | 13 |
| 75 | 25 |
| 100 | 40 |

The PhMeSiCl$_2$ selectivity as used herein is defined as the mass ratio of PhMeSiCl$_2$ to Ph$_2$MeSiCl, as described in Equation 3. The yield (e.g., weight percentage) of PhMeSiCl$_2$ and Ph$_2$MeSiCl present in the reaction product mixture that exits the PFR is measured using gas chromatography (GC). More specifically, the area under the peak in the gas chromatograph associated with each of the products is multiplied by its corresponding response factor, and then normalized accordingly.

$$\text{Selectivity} = \frac{\text{wt \% PhMeSiCl}_2}{\text{wt \% Ph}_2\text{MeSiCl}} \quad \text{Eq. 3}$$

Figure 5:
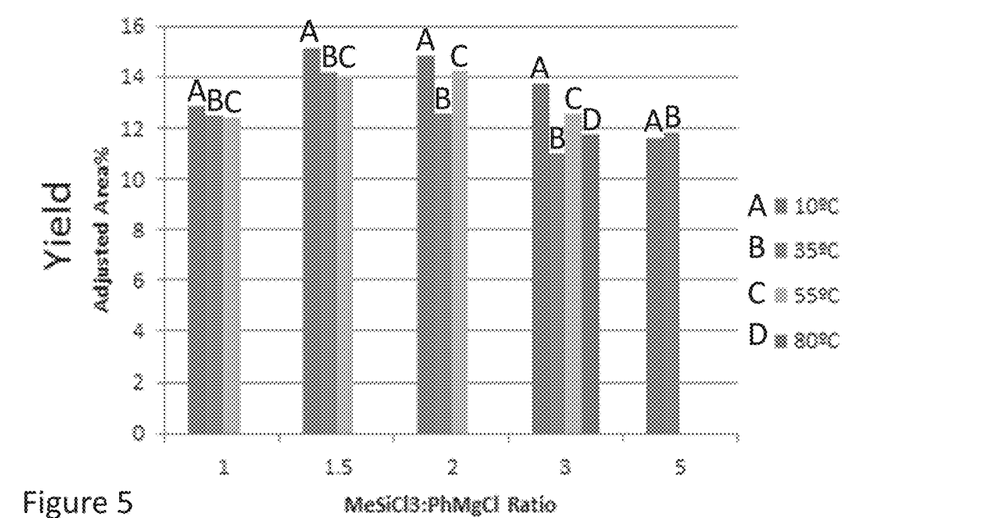
FIG. 5 is a graph of $PhMeSiCl_2$ Yield (wt. %) obtained at various temperatures using PFR configuration C1 plotted as a function of $MeSiCl_3$ to PhMgCl mass ratio.
Figure 6:
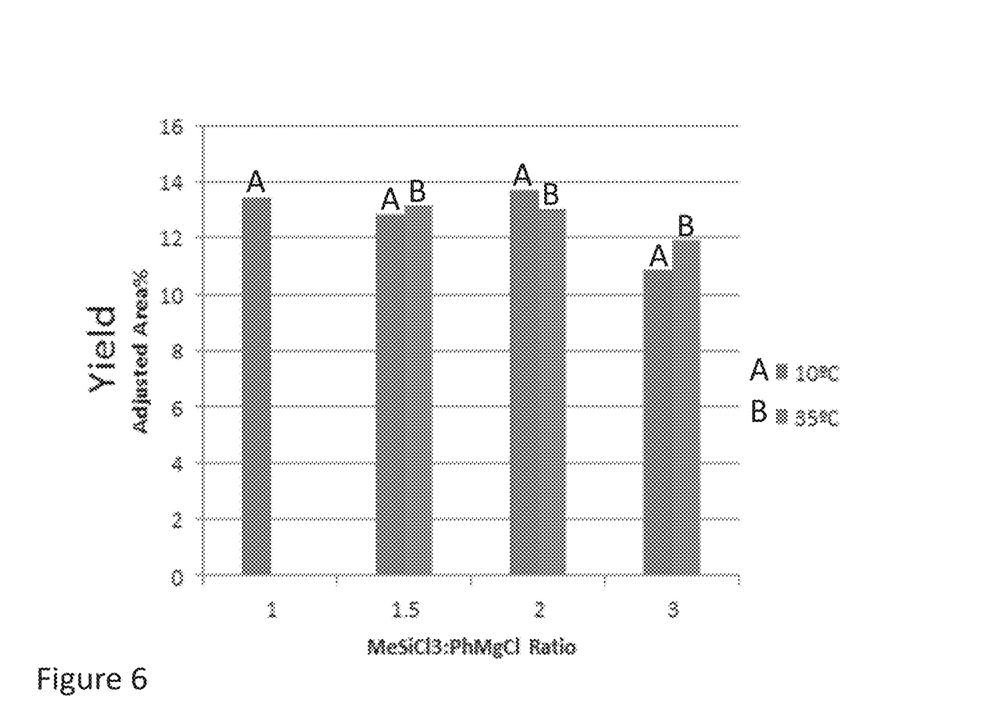
FIG. 6 is a graph of $PhMeSiCl_2$ yield (wt. %) obtained at various temperatures using PFR configuration C2 plotted as a function of $MeSiCl_3$ to PhMgCl mass ratio.

The yield (weight %) of PhMeSiCl$_2$ obtained in the various experimental runs are provided in FIG. 5 for PFR configuration C1 and in FIG. 6 for PFR configuration C2. In each of the runs conducted using PFR configuration C1, the yield of PhMeSiCl$_2$ ranged between about 11% and 15% (see FIG. 5). A greater yield is obtained for runs conducted at lower temperature (e.g., about 10° C.) and for mass ratios of MeSiCl$_3$ to PhMgCl between about 1.5:1 and 3:1 (see FIG. 5). In each of the experimental runs conducted using PFR configuration 2, the yield of PhMeSiCl$_2$ ranged between about 11% and 13% (see FIG. 6).

Figure 7:
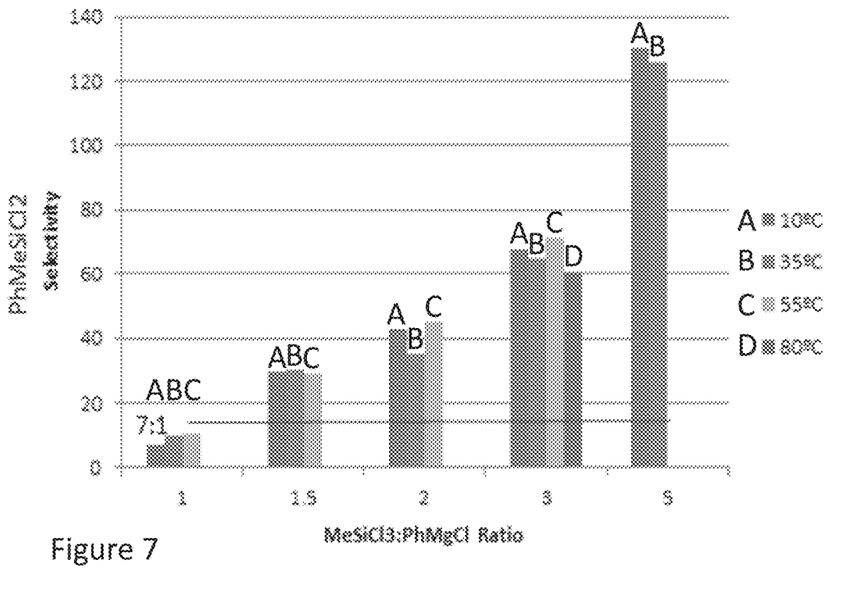
FIG. 7 is a graph of $PhMeSiCl_2$ selectivity obtained at various temperatures using PFR configuration C1 plotted as a function of $MeSiCl_3$ to PhMgCl mass ratio.
Figure 8:
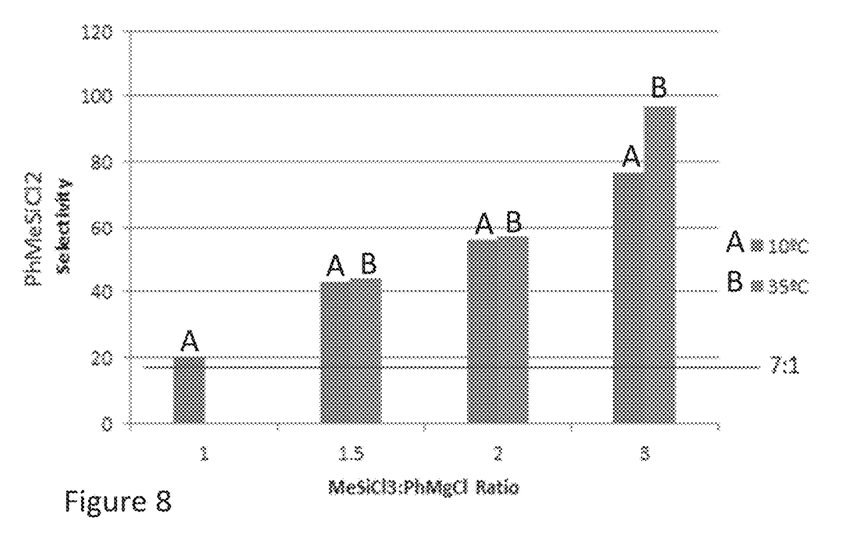
FIG. 8 is a graph of $PhMeSiCl_2$ selectivity obtained at various temperatures using PFR configuration C2 plotted as a function of $MeSiCl_3$ to PhMgCl mass ratio.

The results obtained for PhMeSiCl$_2$ selectivity from the various experimental runs are provided in Table 4 and FIG. 7 for PFR configuration C1 and in Table 5 and FIG. 8 for PFR configuration 2. The data reported in these tables and figures is obtained from the sample taken during the last pass through the reactor at each experimental condition under the assumption that the reaction had reached a steady state by this point. As the mass ratio of MeSiCl$_3$ to PhMgCl increases, the PhMeSiCl$_2$ selectivity is also observed to increase in reactions conducted in either PFR configurations C1 (Table 4; FIG. 7) or C2 (Table 5, FIG. 8). In addition, a trend towards increasing PhMeSiCl$_2$ selectivity as the temperature increases is also observed in runs conducted using PFR configuration 2 (see Table 5; FIG. 8). When the mass ratio of MeSiCl$_3$ to PhMgCl is 1.5:1 or greater, the use of either PFR configuration C1 or C2 results in a PhMeSiCl$_2$ selectivity that is substantially larder than the 7:1 ratio obtained using a conventional process (see FIG. 7 or 8)

TABLE 4

PhMeSiCl$_2$ Selectivity for PFR Configuration 1

| PhMeSiCl2 Selectivity | | Temperature | | | |
|---|---|---|---|---|---|
| | | 10° C. | 35° C. | 55° C. | 80° C. |
| MeSiCl3 to PhMgCl Ratio | 1:1 | 7.36 | 9.67 | 10.66 | |
| | 1.5:1 | 29.73 | 30.07 | 29.15 | |
| | 2:1 | 43.05 | 35.27 | 44.82 | |
| | 3:1 | 67.6 | 64.67 | 71.57 | 60.25 |
| | 5:1 | 130.43 | 126.03 | | |

TABLE 5

PhMeSiCl$_2$ Selectivity for PFR Configuration 2

| PhMeSiCl2 Selectivity | | Temperature | |
|---|---|---|---|
| | | 10° C. | 35° C. |
| MeSiCl3 to PhMgCl Ratio | 1:01 | 20.09 | |
| | 1.5:1 | 43.18 | 44.1 |
| | 2:01 | 55.83 | 57.06 |
| | 3:01 | 76.72 | 96.96 |

Figure 9:
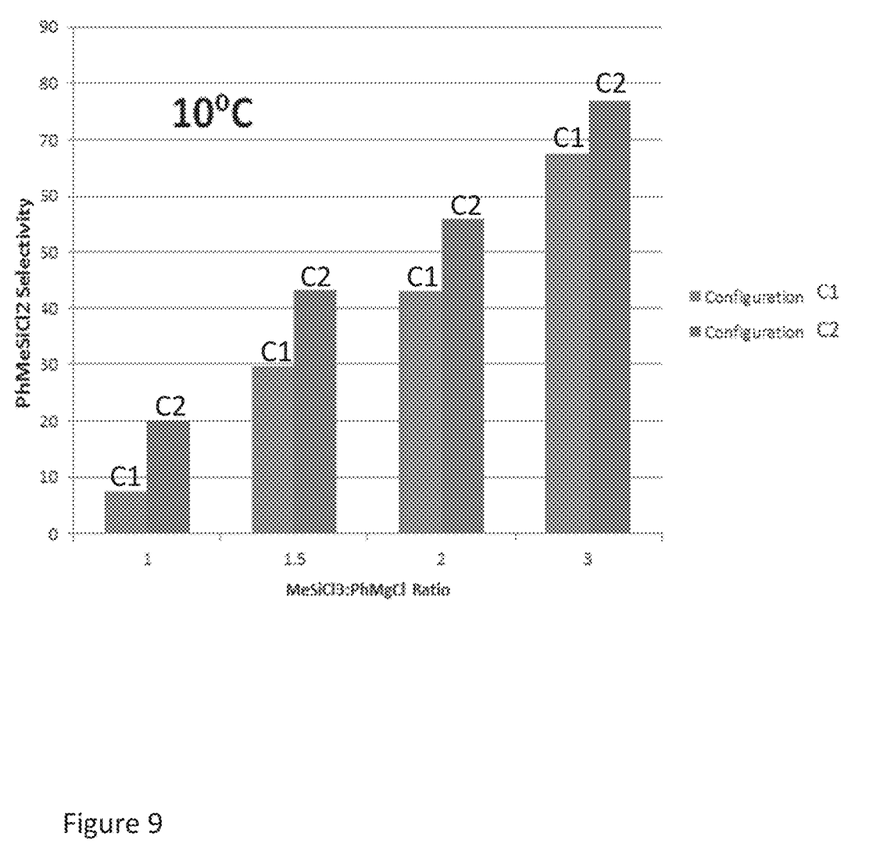
FIG. 9 is a graph of $PhMeSiCl_2$ selectivity obtained from experimental runs conducted at 10° C. in PFR configurations C1 and C2 plotted as a function of $MeSiCl_3$ to PhMgCl mass ratio.

Referring now to FIG. 9, the PhMeSiCl$_2$ selectivity obtained from experimental runs conducted at 10° C. in PFR configurations C1 and C2 are plotted as a function of MeSiCl$_3$ to PhMgCl mass ratio. The increased residence time for the reaction to occur in PFR configuration C2 as compared to the PFR configuration C1 results in an increase in PhMeSiCl$_2$ selectivity.

Figure 10:
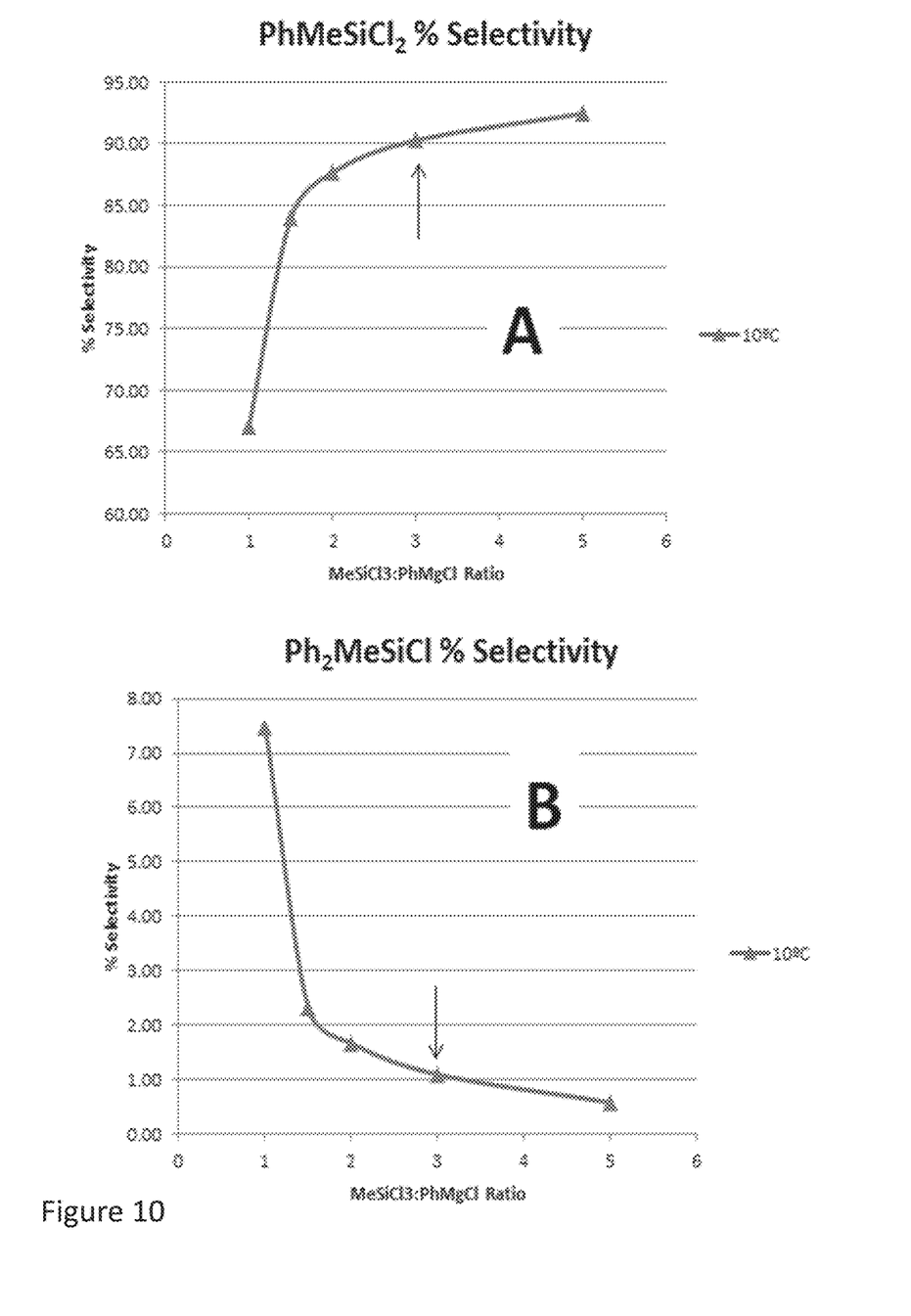
FIG. 10A is a graph of molar % selectivity for $PhMeSiCl_2$ obtained for experimental runs conducted at a temperature of 10° C. in PFR configuration C1 plotted as a function of $MeSiCl_3$ to PhMgCl ratio.
FIG. 10B is graph of molar % selectivity for $PhMeSiCl_2$ obtained for experimental runs conducted at a temperature of 10° C. in PFR configuration C2 plotted as a function of $MeSiCl_3$ to PhMgCl ratio.

In addition to PhMeSiCl$_2$ selectivity, the molar % selectivity for forming PhMeSiCl$_2$ and/or Ph$_2$MeSiCl in the reaction can also be determined according to Equation 4. For the experimental runs conducted using the Corning® Advanced Flow Glass Reactor™ as the PFR 5, the calculation of the molar % selectivity is consistent between the various reaction temperatures and shows very little variation. The molar % selectivity calculated for reactions conducted at a temperature of 10° C. is plotted in FIG. 10(A&B) as a function of MeSiCl$_3$ to PhMgCl ratio. At a 3:1 MeSiCl$_3$ to PhMgCl ratio, the reactor achieves approximately 90% selectivity of PhMeSiCl$_2$ and 1% selectivity of Ph$_2$MeSiCl. As the MeSiCl$_3$ to PhMgCl ratio increases, the molar selectivity of PhMeSiCl$_2$ and Ph$_2$MeSiCl begins to plateau, indicating that the reaction is reaching maximum efficiency as the PhMgCl becomes more and more dilute.

$$\text{Molar \% Selectivity}_i = \frac{\text{mol}_i}{\text{mol}_{PhMgCl,reacted}} * 100\% \quad \text{Eq. 4}$$

Additionally, the PhMgCl % conversion can also be calculated according to Equation 5. The PhMgCl % conversion is calculated for each of the experimental runs conducted using the Corning® Advanced Flow Glass Reactor™ 5 and summarized in Tables 6 and 7. The results obtained at various temperatures and MeSiCl$_3$ to PhMgCl ratios for reactions conducted in the PFR Configuration C1 system are summarized in Table 6. The results obtained at various temperatures and MeSiCl$_3$ to PhMgCl ratios for reactions conducted in the PFR Configuration C2 system are summarized in Table 7. The tabulated results in both Tables 6 and 7 confirm that all of the Grignard reagent reacted, even at a 1:1 ratio of MeSiCl$_3$ to PhMgCl and a short 4.8 second residence time. However, it is noted that the error associated with this calculation is about ±20%.

$$\text{\% Conversion} = \frac{\text{mol}_{PhMgCl\ reacted}}{\text{mol}_{PhMgCl\ fed}} * 100\% \quad \text{Eq. 5}$$

TABLE 6

PhMgCl % Conversion for PFR Configuration C1

| PhMgCl % Conversion | | Temperature | | | |
|---|---|---|---|---|---|
| | | 10° C. | 35° C. | 55° C. | 80° C. |
| MeSiCl3 to PhMgCl Ratio | 1:1 | 125.54 | 116.71 | 113.15 | |
| | 1.5:1 | 125.46 | 118.09 | 118.45 | |
| | 2:1 | 124.63 | 109.12 | 119.43 | |
| | 3:1 | 124.13 | 98.02 | 106.66 | 85.22 |
| | 5:1 | 121.58 | 124.5 | | |

TABLE 7

PhMgCl % Conversion for PFR Configuration C2

| PhMgCl % Conversion | | Temperature | |
|---|---|---|---|
| | | 10° C. | 35° C. |
| MeSiCl3 to PhMgCl Ratio | 1:01 | 106.42 | |
| | 1.5:1 | 100.54 | 99.96 |
| | 2:01 | 112.61 | 102.84 |
| | 3:01 | 94.39 | 102.91 |

The foregoing description of various forms of the invention has been presented for purposes of illustration and description. It is not intended to be exhaustive or to limit the invention to the precise forms disclosed. Numerous modifications or variations are possible in light of the above teachings. The forms discussed were chosen and described to provide the best illustration of the principles of the invention and its practical application to thereby enable one of ordinary skill in the art to utilize the invention in various forms and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A method of making dialkyl-, diaryl-, or alkylaryl-dihalosilanes with a high degree of selectivity in a Grignard coupling reaction, the method comprising the steps of:
   providing a reactor, the reactor selected as one from the group of a plug flow reactor (PFR), a continuous tube reactor (CTR), a piston flow reactor, and more than one continuous stirred tank reactor (CSTR) connected in series;
   providing a hydrocarbon solvent stream at a predetermined flow rate to the reactor;
   providing an alkyl- or aryl-trihalosilane stream at a predetermined flow rate to the reactor;
   providing a Grignard reagent stream comprising an alkyl- or aryl-magnesium halide at a predetermined flow rate to the reactor;
   allowing the solvent stream, alkyl- or aryl-trihalosilane stream, and Grignard reagent stream to combine to form a combined reactant stream;
   wherein the flow rate of the solvent stream, alkyl- or aryl-trihalosilane stream, and the Grignard reagent stream are selected so that the mass ratio of the alkyl- or aryl-trihalosilane to the Grignard reagent in the combined reactant stream is greater than or equal to 1.5:1 and the mass ratio of the solvent to the Grignard reagent in the combined reactant stream is greater than or equal to 3:1;
   allowing the combined reactant stream to react at a temperature from 10° C. to 80° C. to form a product mixture comprising $R_2SiX_2$, $R_3SiX$, and a salt, wherein each R is independently selected to be an alkyl or aryl group, X is a halogen group, and the mass ratio of $R_2SiX_2$ to $R_3SiX$ in the product mixture is greater than 7:1; and
   optionally, collecting the product mixture.

2. The method according to claim 1, wherein the reactor is a PFR comprising at least one fluidic module.

3. The method according to claim 1, wherein the method further comprises the steps of:
   measuring a baseline pressure drop across the reactor prior to starting the Grignard reaction;
   monitoring the pressure drop across the reactor during the course of the Grignard reaction; and comparing the pressure drop across the reactor monitored during the course of the Grignard reaction to the baseline pressure drop in order to determine a change in the pressure drop;
   wherein the change in pressure drop provides a measurement for the degree to which the reactor is plugged by salt that has agglomerated and settled in the reactor or that has deposited on the walls in the reactor.

4. The method according to claim 3, wherein the method further comprises the steps of:
   stopping the Grignard reaction;
   removing the salt plugging the reactor; and
   restarting the Grignard reaction.

5. The method according to claim 4, wherein removing the salt plugging the reactor further comprises the steps of:
   isolating the plugged portion of the reactor from the rest of the reactor;
   flushing hydrocarbon solvent through the isolated portion of the reactor to remove the alkyl- or aryl-trihalosilane;
   flushing water through the isolated portion of the reactor until all the salts are removed;
   flushing an alcohol through the isolated portion of the reactor to remove any residual water;
   flushing the hydrocarbon solvent through the isolated portion of the reactor again to purge the alcohol from the isolated portion; and
   reestablishing contact between the isolated portion of the reactor and the rest of the reactor.

6. The method according to claim 1, wherein the combined reactant stream has a flow rate that is predetermined based on the size of the reactor such that the average amount of time that the combined reactant stream resides in the reactor is less than 30 seconds.

7. The method according to claim 6, wherein the residence time for the combined reactant stream in the reactor is less than 20 seconds.

8. The method according to claim 1, wherein the mass ratio of solvent to Grignard reagent is greater than 5:1.

9. The method according to claim 1, wherein the mass ratio of $R_2SiX_2$ to $R_3SiX$ in the product mixture is greater than 12:1.

10. The method according to claim 1, wherein the Grignard reagent stream is a solution comprising the Grignard reagent dispersed in a solvent;
    wherein the amount of Grignard reagent present in the solution is less than 75 wt. % based on the overall weight of the solution.

11. The method according to claim 1, wherein the solvent is toluene, the Grignard reagent is phenylmagnesium chloride (PhMgCl), the alkyl- or aryl-trihalosilane is methyltrichlorosilane ($MeSiCl_3$), and the product mixture formed comprises $PhMeSiCl_2$, $Ph_2MeSiCl$, and $MgCl_2$.

* * * * *